US007982072B2

(12) United States Patent
Müller et al.

(10) Patent No.: US 7,982,072 B2
(45) Date of Patent: Jul. 19, 2011

(54) PROCESS FOR THE OBTENTION OF PURIFIED HEPTAFLUOROPROPANE

(75) Inventors: Thomas Müller, Bad Wimpfen (DE); Dominique Balthasart, Brussels (BE); Bernd Kutzner, Kelkheim (DE)

(73) Assignee: Solvay S.A., Brussels (BE)

( * ) Notice: Subject to any disclaimer, the term of this patent is extended or adjusted under 35 U.S.C. 154(b) by 0 days.

(21) Appl. No.: 12/965,177

(22) Filed: Dec. 10, 2010

(65) Prior Publication Data

US 2011/0081302 A1  Apr. 7, 2011

Related U.S. Application Data

(60) Division of application No. 12/325,539, filed on Dec. 1, 2008, now Pat. No. 7,872,162, which is a division of application No. 11/782,341, filed on Jul. 24, 2007, now Pat. No. 7,459,591, which is a continuation of application No. 10/488,812, filed as application No. PCT/EP02/10381 on Sep. 5, 2002, now abandoned.

(30) Foreign Application Priority Data

Sep. 7, 2001  (EP) .................................... 01203374

(51) Int. Cl.
*C07C 19/08* (2006.01)
*C07C 17/00* (2006.01)
(52) U.S. Cl. ..................... 570/134; 570/124; 570/181
(58) Field of Classification Search .................. 570/124, 570/134, 181
See application file for complete search history.

(56) References Cited

U.S. PATENT DOCUMENTS

| 5,475,169 A | 12/1995 | Hopp et al. |
| 5,918,481 A | 7/1999 | Pham et al. |

FOREIGN PATENT DOCUMENTS

| EP | 0 512 502 | 11/1992 |
| WO | WO-98/37043 | 8/1998 |
| WO | WO-99/26907 | 6/1999 |
| WO | WO-01/66498 | 9/2001 |

*Primary Examiner* — Jafar Parsa
(74) *Attorney, Agent, or Firm* — Connolly Bove Lodge & Hutz LLP

(57) ABSTRACT

Process for the obtention of HFC-227ea having a reduced content of organic impurities, comprising at least subjecting a crude HFC-227ea to two distillation steps at different pressures.

11 Claims, No Drawings

PROCESS FOR THE OBTENTION OF PURIFIED HEPTAFLUOROPROPANE

RELATED APPLICATIONS

This application is a divisional of U.S. patent application Ser. No. 12/325,539, filed Dec. 1, 2008 now U.S. Pat. No. 7,872,162, which is a divisional of U.S. patent application Ser. No. 11/782,341, filed Jul. 24, 2007, now U.S. Pat. No. 7,459,591, which is a continuation of U.S. patent application Ser. No. 10/488,812, filed Mar. 5, 2004 now abandoned, which is a National Stage Application of International Application No. PCT/EP02/10381, filed Sep. 5, 2002, (all of the above applications are incorporated by reference in their entirety for all useful purposes) which claims benefit to Europe Application No. EP 01203374.2, filed Sep. 7, 2001.

The present invention concerns a process for the obtention of purified 1,1,1,2,3,3,3-heptafluoropropane (HFC-227ea).

HFC-227ea is useful in particular as environmentally-friendly fire-extinguishing agent and as propellant, notably for pharmaceutical aerosols.

The industrial production of HFC-227ea frequently provides, however, a product which comprises saturated and unsaturated impurities. As such impurities are often toxic, strict standards for the concentration of impurities, in particular unsaturated impurities are likely to be adopted for HFC-227ea for pharmaceutical applications.

In EP-0512502-A2 it was proposed to reduce or eliminate the olefin content in HFC-227ea by reaction with an alcohol in the presence of a base. While this process provides outstanding results for the elimination of olefins in HFC-227ea, it requires addition of further chemical compounds to the crude HFC-227ea.

Accordingly, it is a purpose of the invention to provide a process for the obtention of HFC-227ea having a reduced content of all kinds of organic impurities and in particular olefinic impurities which does not require addition of further chemical compounds to the crude HFC-227ea. In particular, it is a purpose of the invention to provide such a process allowing for the obtention of HFC-227ea having a purity suitable for use in pharmaceutical applications, especially as propellant for inhalation aerosols.

In consequence, the invention concerns a process for the obtention of 1,1,1,2,3,3,3-heptafluoropropane (HFC-227ea) having a reduced content of organic impurities, which comprises
(a) subjecting a crude HFC-227ea containing organic impurities to at least two distillations steps, consisting of a high pressure distillation step and a low pressure distillation step carried out at a pressure of at least 1 bar lower than the high pressure distillation step and
(b) recovering HFC 227-ea having a reduced content of organic impurities.

The process according to the invention makes it possible to achieve an efficient separation of organic impurities, in particular of the olefinic impurities from HFC-227ea by a physical method. The process can be carried out in an easy manner and allows for use of steam-heating/water-cooling. In a totally unexpected manner, the process is sufficiently efficient to allow for the use of the obtained HFC-227ea in pharmaceutical applications. The process does not involve addition of further chemical compounds to the crude HFC-227ea. This is particularly advantageous in the manufacture of HFC-227ea for pharmaceutical applications, as all compounds used in manufacture of a pharmaceutical product must be examined as to their toxicity and notified in regulatory procedures.

The purity of the HFC-227ea obtained in the process according to the invention is generally equal to or greater than 99.9% wt. Often this purity is equal to or greater than 99.95% wt. Preferably, it is equal to or greater than 99.99% wt. The HFC-227ea obtained in the process preferably contains less than 5 ppm of any individual olefinic impurity.

The term "low-boiling impurity" is understood to denote an impurity exhibiting, at the pressure of the distillation in the presence of HFC-227ea, a boiling point lower than the boiling point of the HFC-227ea. The term "high-boiling impurity" is understood to denote an impurity exhibiting, at the pressure of the distillation in the presence of HFC-227ea, a boiling point greater than the boiling point of the HFC-227ea.

The pressure in the high pressure distillation is generally at most 30 bar. It is often at most 20 bar. Preferably, the pressure is at most 12 bar. It is more preferably at most 11.5 bar. The pressure in the high pressure distillation is generally at least 6 bar. Often, this pressure is at least 7.5 bar. It is preferably at least 9.5 bar. Generally, a fraction comprising low boiling impurities is drawn off from the high pressure distillation step. The low boiling impurities are thereby removed from the HFC-227ea. Typical low-boiling organic impurities include saturated or insaturated fluorocarbons comprising 1, 2, 3 or 4 carbon atoms. More particularly, low-boiling organic impurities include saturated or unsaturated (hydro)fluorocarbons i.e. organic compounds consisting of carbon, fluorine and optionally hydrogen, comprising 1, 2 or 3 carbon atoms. Hexafluoropropylene is a specific example of a low-boiling organic impurity.

The pressure in the low pressure distillation, is generally at least 1 bar. It is often at least 4 bar. It is preferably at least 6 bar. It is more preferably at least 7 bar. The pressure in the low pressure distillation is at generally at most 12 bar. Preferably this pressure is at most 10 bar. Generally, a fraction comprising high boiling impurities is drawn off from the low pressure distillation. The high boiling impurities are thereby removed from the HFC-227ea. Typical high-boiling organic impurities include saturated or unsaturated (hydro)fluorocarbons comprising at least 5 carbon atoms and (hydro)chlorofluorocarbons comprising preferably at least two carbon atoms. More particularly, high-boiling organic impurities include saturated or unsaturated (hydro)fluorocarbons i.e. organic compounds consisting of carbon, fluorine and optionally hydrogen, comprising at least 6 carbon atoms. Hexafluoropropylene dimers of general formula C6F12 are specific examples of high-boiling organic impurities.

Another type of high-boiling organic impurities includes organic compounds comprising at least one heteroatom, which is preferably selected from oxygen and nitrogen. Generally, these compounds also contain at least one fluorine atom. Mention may be made, for example of fluorinated ethers comprising from 2 to 10 carbon atoms.

In the present description, any reference to the pressure corresponds to the absolute pressure, measured at the top of the distillation column.

The pressure difference between the high pressure distillation step and the low pressure distillation step is at least 1 bar. Preferably, this difference is at least 2 bar. A pressure difference of about 2.5 bar is particularly preferred. Generally, the pressure difference between the high pressure distillation step and the low pressure distillation step is at most 29 bar. Preferably, this difference is at most 10 bar. A pressure difference of at most 5 bar is particularly preferred.

The temperature at which the high or the low pressure distillation is carried out corresponds approximately to the boiling point of the HFC-227ea at the pressure chosen for the respective distillation.

In a first embodiment of the process according to the invention the low pressure distillation step is carried out before the high pressure distillation step.

In a second embodiment of the process according to the invention, which is preferred, the low pressure distillation step is carried out after the high pressure distillation step. In the second embodiment it is possible to recover the HFC-227ea having a reduced content of organic impurities from the top of the low pressure distillation. This mode of recovery is particularly advantageous, as it allows to minimise and even completely eliminate the risk of contamination of the HFC-227ea by optionally present corrosion products of column material.

Each of the two distillation steps can be carried out in one or more distillation columns. Use will preferably be made of a single column per distillation step.

The distillation columns which can be used in the process according to the invention are known per se. Use may be made, for example, of conventional plate columns or plate columns of dual-flow type or alternatively of columns with bulk or structured packing.

The number of theoretical plates in the high pressure distillation is generally at least 10. It is often at least 20. A number of at least 35 gives good results.

The number of theoretical plates in the low pressure distillation is generally at least 5. It is often at least 15. A number of at least 30 gives good results.

The mass reboiling ratio in the high pressure distillation is generally at least 1. Frequently, the mass reboiling ratio is at least 3. More frequently, the mass reboiling ratio is at least 8. A mass reboiling ratio of at least 10 is preferred. The mass reboiling ratio in the high pressure distillation is generally at most 100. Frequently, the mass reboiling ratio is at most 50. More frequently, the mass reboiling ratio is at most 30. A mass reboiling ratio of at most 25 is preferred.

The mass reflux ratio in the low pressure distillation is generally at least 2. Frequently, the mass reflux ratio is at least 4. A mass reflux ratio of at least 5 is preferred. The mass reflux ratio in the low pressure column is generally at most 50. Frequently, the mass reflux ratio is at most 30. A mass reflux ratio of at most 20 is preferred.

In a particular embodiment, the mass ratio in the high pressure distillation of the feed of crude HFC-227ea to the fraction comprising said low-boiling organic impurities withdrawn from said high pressure distillation is kept in a range from 1 to 100. Preferably this mass ratio is kept in a range from 3 to 60. In a particularly preferred embodiment the mass ratio is controlled so as to display a deviation from the desired mass ratio of at most 10%. Preferably this deviation is at most 5%. Most preferably the deviation is at most 3%.

The high and low pressure distillations can be operated in continuous or discontinuous mode. In a preferred embodiment, the fraction comprising low-boiling organic impurities is continuously withdrawn from the high pressure distillation. The latter embodiment is used in a particularly advantageous manner, when the crude HFC-227ea contains a low amount of low-boiling organic impurities.

Typical examples of crude HFC-227ea which can be used in the process according to the invention, have a content of low-boiling organic impurities of 1% by weight or less. Often this content is 0.5% by weight or less. Preferably, this content is 0.3% by weight or less.

Typical examples of crude HFC-227ea which can be used in the process according to the invention have a purity of at least 95% by weight. Often the purity is greater than or equal to 99% by weight. Preferably, the purity is greater than or equal to 99.5% by weight.

The crude HFC-227ea can be obtained for example, through hydrofluorination of hexafluoropropylene, through hydrofluorination of suitable halofluoropropanes or through hydrogenation of 2-chloroheptafluoropropane. Advantageously, the crude HFC-227ea has been obtained by a reaction comprising use of hexafluoropropylene as a starting material. Preferably, the crude HFC-227ea has been obtained by reaction of hexafluoropropylene with hydrogen fluoride, preferably in the presence of a hydrofluorination catalyst.

If necessary, the crude HFC-227ea product obtained in reactions such as mentioned hereinbefore, may be worked-up by operations such as washing and rough-distillation to achieve the preferred purities for the crude HFC-227ea which is introduced into the process according to the invention.

In a still further embodiment, the crude HFC-227ea also comprises water. In this embodiment of the process according to the invention, the fraction comprising low-boiling organic impurities, which can be withdrawn from the high pressure distillation step, also comprises water which is thereby removed from the crude HFC-227ea. It should be understood that the specific preferences and general descriptions of the process according to the invention specifically apply to the present further embodiment. It has been surprisingly found that water, which normally should be expected to be a high boiler with regard to HFC-227ea at all distillation pressures, forms an azeotrope with low boiling organic impurities and HFC-227ea, thus enabling for efficient water removal from HFC-227ea. Water removal is especially advantageous when a HFC-227ea suitable for pharmaceutical aerosols is desired, as the presence of water might influence in an undesirable way, the solubility and crystal growth of medicaments to be dissolved or suspended in the HFC-227ea-comprising propellant.

Basically, the thermodynamic state of a fluid is defined by four interdependent variables: the pressure (P), the temperature (T), the composition of the liquid phase (X) and the composition of the gas phase (Y). A true azeotrope is a specific system of 2 or more components for which, at a given temperature and a given pressure, the composition of the liquid phase X is exactly equal to the composition of the gas phase Y. A pseudo-azeotrope is a system of 2 or more components for which, at a given temperature and a given pressure, X is substantially equal to Y. In practice, this means that the constituents of such azeotropic and pseudo-azeotropic systems cannot be readily separated by distillation.

For the purposes of the present invention, the expression "pseudo-azeotropic mixture" means a mixture of two constituents whose boiling point (at a given pressure) differs from the boiling point of the true azeotrope by a maximum of 0.5° C. Mixtures whose boiling point differs from the boiling point of the true azeotrope by a maximum of 0.2° C. are preferred. Mixtures whose boiling point differs from the boiling point of the true azeotrope by a maximum of 0.1° C. are particularly preferred.

The invention concerns also an azeotropic or pseudo-azeotropic mixture comprising HFC-227ea and water. The azeotropic or pseudo-azeotropic mixture according to the invention consists generally, at a pressure of 10.5 bar essentially of HFC-227ea and at most 500 mg/kg of water. Preferably the water content in the azeotropic or pseudo-azeotropic mixture at 10.5 bar is at most 300 mg/kg. A water content in the azeotropic or pseudo-azeotropic mixture at 10.5 bar of at most 200 mg/kg is particularly preferred. The azeotropic or pseudo-azeotropic mixture according to the invention consists generally, at a pressure of 10.5 bar essentially of HFC-227ea and at least 20 mg/kg of water. Preferably the water content in the azeotropic or pseudo-azeotropic mixture at 10.5 bar is at least 50 mg/kg. A water content in the azeotropic or pseudo-azeotropic mixture at 10.5 bar of at least 100 mg/kg is particularly preferred.

The azeotropic or pseudo-azeotropic mixture according to the invention consists generally, at a pressure of 1 bar essentially of HFC-227ea and at most 50 mg/kg of water. Preferably the water content in the azeotropic or pseudo-azeotropic mixture at 1 bar is at most 30 mg/kg. The azeotropic or pseudoazeotropic mixture according to the invention consists generally, at a pressure of 1 bar essentially of HFC-227ea and at least 5 mg/kg of water. Preferably the water content in the azeotropic or pseudo-azeotropic mixture at 10.5 bar is at least 10 mg/kg.

In a particular embodiment the azeotropic or pseudo-azeotropic mixture according to the invention comprises in addition organic impurities which are low-boiling with respect to HFC-227ea at the pressures of the high pressure distillation step such as described above.

The azeotropic or pseudo-azeotropic mixture according to the invention can be used to remove water and optionally low boiling organic impurities from HFC-227ea.

The example given below is intended to illustrate, without implied limitation, the process according to the invention.

EXAMPLE

A crude HFC-227ea obtained by hydrofluorination of hexafluoropropene having a purity of about 99.8% wt. and containing 0.1% wt. low-boiling organic impurities including hexafluoropropylene, 0.05% wt. high-boiling organic impurities including $C_6F_{12}$ and water has been purified according to the process according to the invention. The crude HFC-227ea was introduced into the high pressure distillation step. The light-boilers were continuously drawn off from the top of the high pressure distillation. An HFC-227ea fraction containing high-boilers was withdrawn from the bottom of the high pressure distillation and introduced into the low pressure distillation. Purified HFC-227ea was withdrawn from the top of the low pressure distillation. The table hereafter indicates the process conditions which were used in the first and low pressure distillation respectively.

|  | High pressure distillation | Low pressure distillation |
| --- | --- | --- |
| Pressure (bar) | 10.5 | 8 |
| Temperature (° C.) | 55 | 45 |
| Reboiling ratio (mass) | 17.5 | — |
| Reflux ratio (mass) | — | 14 |
| Theoretical plates | 40 | 33 |
| Mass ratio (feed crude HFC-227ea/low boiler fraction drawn off) | 30 | — |

The obtained purified HFC-227ea had a purity of greater than 99.99% vol determined by gas chromatography. The content of any olefinic impurities was less than 5 ppm. The HFC-227ea contained less than 10 ppm of water determined by Karl-Fischer method.

The invention claimed is:

1. An azeotropic or pseudo-azeotropic mixture at 10.5 bar consisting essentially of HFC-227ea and water wherein the water content is at most 500 mg/kg and wherein the pseudo-azeotropic mixture means a mixture of two constituents whose boiling point at a given pressure differs from the boiling point of the true azeotrope by a maximum of 0.5° C.

2. The azeotropic or pseudo-azeotropic mixture according to claim 1, wherein the water content is at most 300 mg/kg.

3. The azeotropic or pseudo-azeotropic mixture according to claim 2, wherein the water content is at most 200 mg/kg.

4. The azeotropic or pseudo-azeotropic mixture according to claim 1, at 10.5 bar consisting essentially of HFC-227ea and water wherein the water content is at least 20 mg/kg.

5. The azeotropic or pseudo-azeotropic mixture according to claim 4, wherein the water content is at least 50 mg/kg.

6. The azeotropic or pseudo-azeotropic mixture according to claim 5, wherein the water content is at least 100 mg/kg.

7. The azeotropic or pseudo-azeotropic mixture according to claim 1, at 1 bar consisting essentially of HFC-227ea and water wherein the water content is at most 50 mg/kg.

8. The azeotropic or pseudo-azeotropic mixture according to claim 7, wherein the water content is at most 30 mg/kg.

9. The azeotropic or pseudo-azeotropic mixture according to claim 1, at 1 bar consisting essentially of HFC-227ea and water wherein the water content is at least 5 mg/kg.

10. The azeotropic or pseudo-azeotropic mixture according to claim 9, wherein the water content is at least 10 mg/kg.

11. The azeotropic or pseudo-azeotropic mixture according to claim 1, comprising in addition organic impurities which are low-boiling with respect to HFC-227ea at a pressure of from more than 9 to 16 bar.

* * * * *